US012636517B2

(12) United States Patent
De Taboada et al.

(10) Patent No.: US 12,636,517 B2
(45) Date of Patent: *May 26, 2026

(54) NON-ABLATIVE PHOTONIC DEVICES AND RELATED METHODS

(71) Applicant: LiteCure, LLC, Newark, DE (US)

(72) Inventors: Luis De Taboada, Carlsbad, CA (US);
Brian Pryor, Newark, DE (US)

(73) Assignee: LiteCure, LLC, New Castle, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/169,811

(22) Filed: Feb. 15, 2023

(65) Prior Publication Data

US 2023/0191148 A1    Jun. 22, 2023

Related U.S. Application Data

(60) Division of application No. 17/303,765, filed on Jun. 7, 2021, now abandoned, which is a continuation of application No. 16/111,735, filed on Aug. 24, 2018, now Pat. No. 11,033,754.

(60) Provisional application No. 62/552,299, filed on Aug. 30, 2017.

(51) Int. Cl.
| | |
|---|---|
| *A61N 5/06* | (2006.01) |
| *G02B 6/42* | (2006.01) |
| *A61N 5/067* | (2006.01) |

(52) U.S. Cl.
CPC ........... *A61N 5/0625* (2013.01); *A61N 5/062* (2013.01); *G02B 6/4204* (2013.01); *G02B 6/4298* (2013.01); *A61N 2005/0628* (2013.01);
*A61N 2005/063* (2013.01); *A61N 2005/0631* (2013.01); *A61N 2005/0651* (2013.01); *A61N 5/067* (2021.08)

(58) Field of Classification Search
CPC .............................. A61N 5/062; A61N 5/0625
See application file for complete search history.

(56) References Cited

U.S. PATENT DOCUMENTS

| | | | |
|---|---|---|---|
| 1,844,247 A | | 2/1932 | Freemon |
| 2,183,726 A | | 12/1939 | Sommer et al. |
| 2,490,074 A | | 12/1949 | Marty |

(Continued)

FOREIGN PATENT DOCUMENTS

| | | |
|---|---|---|
| WO | WO 10/006082 | 1/2010 |
| WO | WO 10/060097 | 5/2010 |

OTHER PUBLICATIONS

Kyocera Corporation, 2007, Single crystal sapphire, product brochure, 8 pp.

(Continued)

*Primary Examiner* — George R Evanisko

(74) *Attorney, Agent, or Firm* — Eversheds-Sutherland (US) LLP

(57) ABSTRACT

A method of delivering light energy to a pathological tissue includes emitting light energy from a first optical element within a cannula, producing a substantially uniform irradiance profile from the light energy within the cannula, transmitting the light energy emitted from the first optical element through a second optical element in thermal contact with a distal end of the cannula to the pathological tissue without ablating the pathological tissue, and conducting thermal energy from the pathological tissue through the second optical element and to the cannula.

10 Claims, 8 Drawing Sheets

(56)       References Cited

U.S. PATENT DOCUMENTS

| | | | |
|---|---|---|---|
| 2,699,771 | A | 1/1955 | Ruttger-Pelli |
| 4,907,132 | A | 3/1990 | Parker |
| 5,336,159 | A | 8/1994 | Cheng |
| 5,415,652 | A | 5/1995 | Mueller et al. |
| 5,591,219 | A | 1/1997 | Dungan |
| 6,056,204 | A | 5/2000 | Glezer et al. |
| 6,063,108 | A | 5/2000 | Salansky et al. |
| 6,066,129 | A | 5/2000 | Larson |
| 6,214,035 | B1 | 4/2001 | Streeter |
| 6,413,268 | B1 | 7/2002 | Hartman |
| 6,620,154 | B1 | 9/2003 | Amirkhanian et al. |
| 6,866,678 | B2 | 3/2005 | Shenderova et al. |
| 6,989,023 | B2 | 1/2006 | Black |
| 7,033,382 | B2 | 4/2006 | Lach |
| 7,052,167 | B2 | 5/2006 | Vandershuit |
| 7,083,580 | B2 | 8/2006 | Bernabei |
| 7,083,581 | B2 | 8/2006 | Tsai |
| 7,144,247 | B2 | 12/2006 | Black |
| 7,264,598 | B2 | 9/2007 | Shin |
| 7,282,037 | B2 | 10/2007 | Cho |
| 7,335,170 | B2 | 2/2008 | Milne et al. |
| 7,344,528 | B1 | 3/2008 | Tu et al. |
| 7,749,178 | B2 | 7/2010 | Imboden et al. |
| 7,762,964 | B2 | 7/2010 | Slatkine |
| 7,783,346 | B2 | 8/2010 | Smith et al. |
| 8,498,506 | B2 | 7/2013 | Smith et al. |
| 8,574,177 | B2 | 11/2013 | Pryor et al. |
| 8,685,010 | B2 * | 4/2014 | McMillan ................ A61B 5/01 |
| | | | 606/17 |
| 8,882,685 | B2 | 11/2014 | Pryor et al. |
| 8,968,221 | B2 | 3/2015 | Pryor et al. |
| 9,358,403 | B2 | 6/2016 | Pryor et al. |
| 9,649,506 | B2 | 5/2017 | Pryor et al. |
| 10,238,889 | B2 | 3/2019 | Pryor et al. |
| 10,675,480 | B2 | 6/2020 | Pryor et al. |
| 11,020,606 | B2 | 6/2021 | Pryor et al. |
| 11,033,754 | B2 * | 6/2021 | De Taboada ........... A61N 5/062 |
| 11,511,128 | B2 | 11/2022 | Pryor et al. |
| 2003/0163068 | A1 | 8/2003 | Kang |
| 2003/0219202 | A1 | 11/2003 | Loebb et al. |
| 2003/0232303 | A1 | 12/2003 | Black |
| 2004/0138727 | A1 | 7/2004 | Taboada et al. |
| 2004/0193235 | A1 | 9/2004 | Altshuler et al. |
| 2004/0193236 | A1 | 9/2004 | Altshuler et al. |
| 2004/0236252 | A1 | 11/2004 | Muzzi et al. |
| 2004/0260209 | A1 | 12/2004 | Ella et al. |
| 2004/0260212 | A1 | 12/2004 | Cho |
| 2006/0235494 | A1 | 10/2006 | Vanderschuit |
| 2006/0253051 | A1 | 11/2006 | Milne et al. |
| 2007/0038206 | A1 * | 2/2007 | Altshuler ........... A46B 15/0036 |
| | | | 606/20 |
| 2007/0073366 | A1 | 3/2007 | Porco |
| 2007/0096118 | A1 | 5/2007 | Mahalingam et al. |
| 2008/0014011 | A1 | 1/2008 | Rossen |
| 2008/0262394 | A1 | 10/2008 | Pryor et al. |
| 2008/0292255 | A1 | 11/2008 | Stevens et al. |
| 2009/0001372 | A1 | 1/2009 | Arik et al. |
| 2009/0234253 | A1 | 9/2009 | Vandenbelt et al. |
| 2009/0248004 | A1 | 10/2009 | Altshuler et al. |
| 2009/0299236 | A1 | 12/2009 | Pryor et al. |
| 2010/0042080 | A1 | 2/2010 | Smith et al. |
| 2010/0286673 | A1 * | 11/2010 | Altshuler ............ A61N 5/0616 |
| | | | 606/9 |
| 2011/0144725 | A1 | 6/2011 | Pryor et al. |
| 2013/0041309 | A1 * | 2/2013 | Siegel .................. A61N 5/0616 |
| | | | 606/17 |
| 2013/0253487 | A1 * | 9/2013 | Liu ...................... A61N 5/0616 |
| | | | 372/50.122 |
| 2014/0316387 | A1 * | 10/2014 | Harris .................. A61B 18/203 |
| | | | 606/9 |
| 2015/0065925 | A1 | 3/2015 | Pryor et al. |
| 2015/0174424 | A1 | 6/2015 | Pryor et al. |
| 2015/0190649 | A1 * | 7/2015 | Gelfand ........... A61M 16/0434 |
| | | | 385/100 |
| 2016/0279440 | A1 | 9/2016 | Pryor et al. |
| 2017/0304646 | A1 | 10/2017 | Pryor et al. |
| 2020/0360713 | A1 | 11/2020 | Pryor et al. |
| 2022/0016440 | A1 | 1/2022 | Taboada et al. |

OTHER PUBLICATIONS

EP Search Report in European App. No. 18851281.8, dated Apr. 23, 2020, 8 pages.

PCT International Search Report and Written Opinion in International Application No. PCT/US2018/047889, dated Oct. 19, 2018, 12 pages.

* cited by examiner

Distal face of sapphire
(Detector size = 8x8mm)

Distal face +10mm
(Detector size = 16x16mm)

Distal face +20mm
(Detector size = 20x20mm)

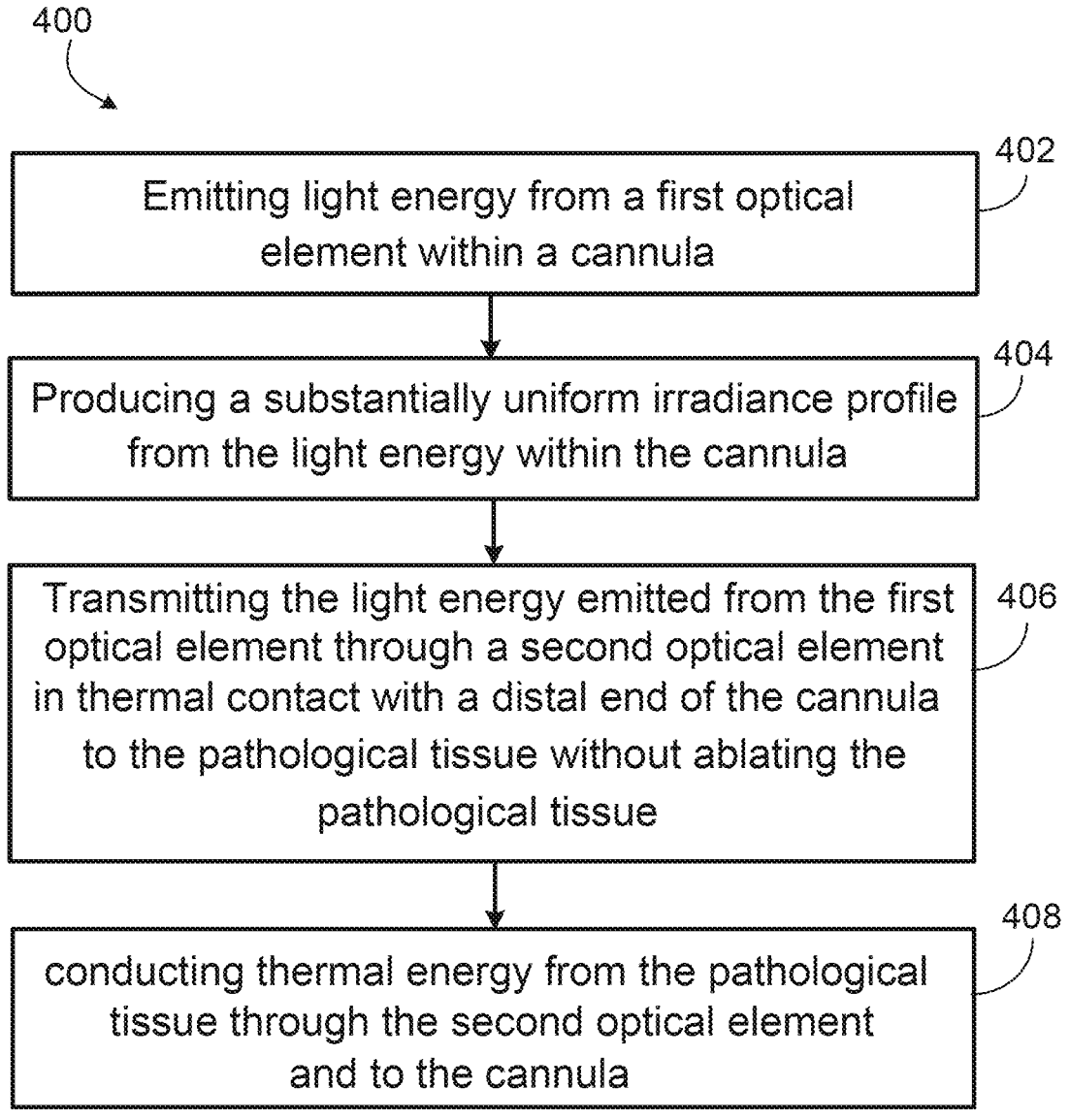

400

Emitting light energy from a first optical element within a cannula · 402

Producing a substantially uniform irradiance profile from the light energy within the cannula · 404

Transmitting the light energy emitted from the first optical element through a second optical element in thermal contact with a distal end of the cannula to the pathological tissue without ablating the pathological tissue · 406 conducting thermal energy from the pathological tissue through the second optical element and to the cannula · 408

FIG. 16

NON-ABLATIVE PHOTONIC DEVICES AND RELATED METHODS

CROSS-REFERENCE TO RELATED APPLICATIONS

This application is a divisional application of U.S. application Ser. No. 17/303,765 filed Jun. 7, 2021, which is a continuation application of U.S. application Ser. No. 16/111,735, filed Aug. 24, 2018, which claims priority to U.S. Provisional Patent Application No. 62/552,299, filed on Aug. 30, 2017 and entitled "Non-ablative Photonic Devices and Related Methods," the entire contents of each of these disclosure are incorporated herein by reference.

TECHNICAL FIELD

This disclosure relates to non-ablative photonic devices and related methods of delivering photonic therapy to pathological tissues.

BACKGROUND

Light energy (e.g., visible light and infrared light in the electromagnetic spectrum from about 400 nm to about 14 μm) can be used to treat various pathological tissues on human patients or other animal bodies. In some instances, light treatments may be invasive and/or include focused, pulsed light energy (e.g., having high peak irradiance and high peak energy), which can ablate tissues. Ablative treatments can potentially harm healthy tissues surrounding pathological tissues. In other instances, light treatments may be invasive and/or include high average irradiances, which may potentially carbonize the tissues (i.e., both pathological tissues and healthy tissues). It is highly desirable to precisely control light energy dosages and thermal energy generated by tissue absorption of light energy to achieve safe and effective therapeutic results.

SUMMARY

In general, this disclosure relates to photonic devices (e.g., light delivery assemblies) for light sources (e.g., lasers) used to deliver non-focused, controlled photonic therapy to pathological tissues in mammals. Such photonic devices are advantageously designed to be non-invasive and accordingly may be used for direct access to certain areas of a body, such as skin or various body cavities. The photonic devices are non-ablative devices, such that the devices can deliver light energy to treat a tissue without vaporizing the tissue, exploding the tissue, burning the tissue, carbonizing the tissue, or otherwise removing or eroding the tissue. Rather, the photonic devices are designed and constructed to radiate light energy in the visible and infrared wavelength ranges onto a human patient or another animal body to destroy a pathological tissue by heating the pathological tissue. The photonic devices can produce uniform irradiance profiles characterized by a substantially constant intensity, such that a pathological tissue irradiated by the light energy can be adequately, uniformly, and gently treated (e.g., heated). Such photonic devices include a cannula and a thermally conductive element (e.g., a rod) secured to a distal end of the cannula. The thermally conductive element is made of a material that can be directly exposed to tissues and bodily fluids, can transmit light energy from a light source to a tissue, and can conduct heat energy from the tissue to the cannula. The thermally conductive element has a shape (e.g., a cylindrical shape) that is optimized according to thermo-dynamics of heat flow such that maximal light energy can be delivered to a surface of a pathological tissue without ablating the tissue. Therefore, maximal light energy can be delivered at any given depth of the pathological tissue to cause photothermal necrosis to destroy the pathological tissue.

Advantageously, the photonic devices can also deliver light energy to nanoparticles or other particles within pathological regions (e.g., tumors or other pathological tissues) to provide photonic therapy. For example, nanoparticles are designed to preferentially accumulate within a pathological tissue and to selectively absorb a wavelength to be used for photonic therapy delivered to the pathological tissue. The nanoparticles can be selectively heated by the light energy and can advantageously destroy the pathological tissue without harming surrounding healthy tissues. In some embodiments, the photonic devices can deliver photonic therapy directly to a pathological tissue (e.g., without the presence of nanoparticles).

In one aspect, a non-ablative photonic device includes a cannula, a first optical element located adjacent a proximal end of the cannula and configured to produce light energy with a substantially uniform irradiance profile, and a second optical element in thermal contact with a distal end of the cannula. The second optical element is configured to transmit the light energy emitted from the first optical element to a pathological tissue located distal to the second optical element and configured to conduct thermal energy from the pathological tissue to the cannula.

Embodiments may include one or more of the following features.

In some embodiments, the first optical element is an optical fiber.

In certain embodiments, the second optical element is a waveguide.

In some embodiments, the second optical element is a cylindrical sapphire rod.

In certain embodiments, the non-ablative photonic device includes a laser that generates the light energy.

In some embodiments, the non-ablative photonic device includes a light-emitting diode (LED) that generates the light energy.

In certain embodiments, the substantially uniform irradiance profile has a non-circular cross-sectional shape.

In some embodiments, the substantially uniform irradiance profile has a hexagonal cross-sectional shape or a square cross-sectional shape.

In certain embodiments, the substantially uniform irradiance profile is transmitted to a distal surface of the second optical element.

In some embodiments, the first optical element terminates near the proximal end of the cannula.

In certain embodiments, the non-ablative photonic device further includes one or more lenses positioned within the cannula between the first optical element and the second optical element and configured to direct the laser beam away from an internal surface of the cannula to limit reflection losses within the cannula.

In some embodiments, the first optical element extends distally into a lumen of the cannula.

In another aspect, a light delivery assembly includes multiple non-ablative photonic devices.

In another aspect, a method of delivering light energy to a pathological tissue includes emitting light energy from a first optical element within a cannula, producing a substantially uniform irradiance profile from the light energy within the cannula, transmitting the light energy emitted from the first optical element through a second optical element in thermal contact with a distal end of the cannula to the pathological tissue without ablating the pathological tissue, and conducting thermal energy from the pathological tissue through the second optical element and to the cannula.

Embodiments may include one or more of the following features.

In some embodiments, the first optical element is an optical fiber.

In certain embodiments, the second optical element is a waveguide.

In some embodiments, the second optical element is a cylindrical sapphire rod.

In certain embodiments, the method further includes generating the light energy with a laser.

In some embodiments, the method further includes generating the light energy with a light-emitting diode (LED).

In some embodiments, the substantially uniform irradiance profile has a non-circular cross-sectional shape.

In certain embodiments, the substantially uniform irradiance profile has a hexagonal cross-sectional shape or a square cross-sectional shape.

In some embodiments, the method further includes transmitting the substantially uniform irradiance profile to a distal surface of the second optical element.

In certain embodiments, the method further includes directing the light energy away from an internal surface of the cannula through one or more lenses positioned within the cannula between the first optical element and the second optical element to limit reflection losses within the cannula.

In some embodiments, the method further includes transmitting the light energy through the second optical element to nanoparticles bound to the pathological tissue.

In some embodiments, the method further includes emitting light energy from a third optical element within a second cannula disposed adjacent the first cannula, producing a second substantially uniform irradiance profile from the light energy within the second cannula, transmitting the light energy emitted from the third optical element through a fourth optical element in thermal contact with a distal end of the second cannula to the pathological tissue to overlap the first and second substantially uniform irradiance profiles beneath a surface of the pathological tissue without ablating the pathological tissue, and conducting thermal energy from the pathological tissue through the fourth optical element and to the second cannula.

Other aspects, features, and advantages will be apparent from the description, the drawings, and the claims.

DESCRIPTION OF DRAWINGS

FIG. 16 is a flowchart illustrating a method of using photonic devices described herein.

DETAILED DESCRIPTION

Figures 1, 2:
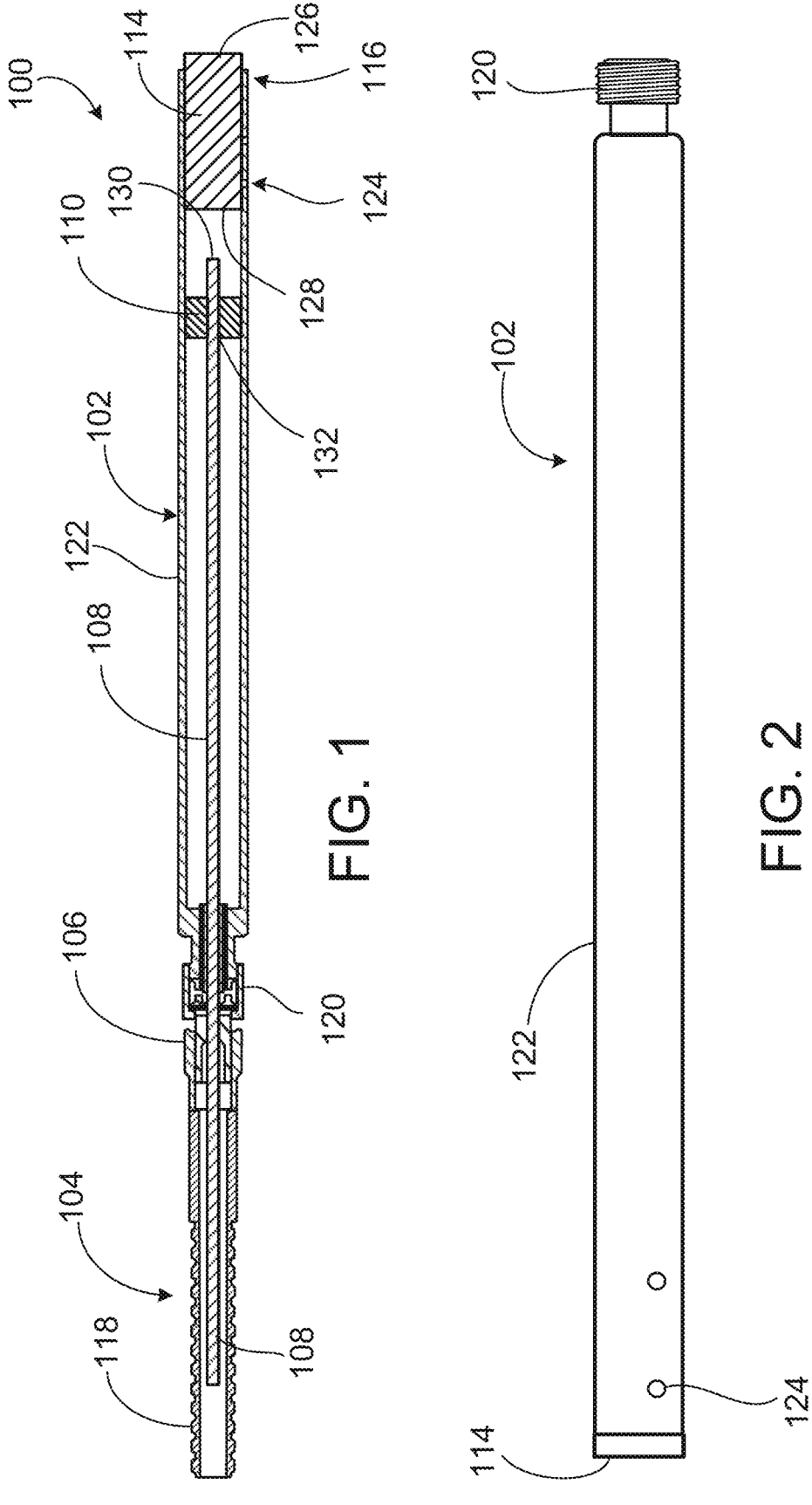
FIG. 1 is a longitudinal cross-sectional view of a photonic device.
FIG. 2 is a perspective view of a cannula and a transmissive element of the photonic device of FIG. 1.

FIG. 1 illustrates a cross-sectional view of an example photonic device 100 designed to deliver photonic therapy (e.g., electromagnetic radiation or light energy) to a pathological tissue on a human or another animal (e.g., a dog or a cat). Example pathological tissues include tumors (e.g., melanomas), lesions, ulcers, bacterial infected tissues (e.g., methicillin-resistant *Staphylococcus aureus* (MRSA)), and other pathological regions. The photonic device 100 is a non-ablative light delivery assembly that is constructed to deliver photonic therapy to particles (e.g., nanoparticles) adjacent (e.g., bound to, positioned on, or positioned within) the pathological tissue and to deliver photonic therapy directly to the pathological tissue, depending on various parameters, such as a wavelength of the light energy, an irradiance at the skin or other external tissue, a surface temperature at the skin or other external tissue, and a treatment or exposure time.

In the depicted embodiment, the photonic device 100 includes a cannula 102 and a fiber optic cable assembly 104. The fiber optic cable assembly 104 includes a ridged outer tubular housing 118, an optical fiber 108 protruding from the tubular housing 118 and extending distally into the cannula 102, and a male connector 106 joining a distal end of the tubular housing 118 with a female connector 120 that forms a proximal end of the cannula 102. The photonic device 100 further includes a fiber support member 110 disposed about the optical fiber 108 within the cannula 102 and an optically transparent, thermally conductive element 114 (e.g., a transmissive rod element that serves as a waveguide) that is secured in thermal contact with a distal end region 116 of the cannula 102.

A distance between an output end 130 (e.g., a distal end) of the optical fiber 108 and a proximal surface 128 of the transmissive element 114 can be adjusted. The tubular housing 118 protects the optical fiber 108 and allows the optical fiber 108 to bend for flexible manipulation of the cannula 102. In some embodiments, the tubular housing 118 and the optical fiber 108 therein have a bend radius in a range of about 10 mm to about 100 mm. The tubular housing 118 and the male connector 106 typically have an assembled length of about 1 m to about 5 m (e.g., about 3 m). The tubular housing 118 typically has an internal diameter of about 1 mm to about 10 mm (e.g., about 3 mm) and typically has an outer diameter of less than about 10 mm. The tubular housing 118 is typically made of one or more materials, including stainless steel. The male connector and the female connector 120 may be SubMiniature version A (SMA) connectors or other types of connectors (e.g., ST connectors) suitable to the application.

Referring to FIGS. 1 and 2, the cannula 102 allows passage of light emitted from the output end 130 of the optical fiber 108 through the optically transparent, transmissive element 114 to a surface of the pathological tissue for photonic treatment. The cannula 102 has a main portion 122 (e.g., a central portion between the female connector 120 and the distal end region 116) that surrounds the output end 130 of the optical fiber 108. The cannula 102 also defines four holes 124 along the distal end region 116 that provide reservoirs for a thermally conductive adhesive substance that may be used to attach the transmissive element 114 to the cannula 102, as will be discussed in more detail below. The holes 124 typically have a diameter of about 0.5 mm to about 3.0 mm (e.g., about 1.0 mm). The cannula 102 is typically made of one or more materials that can efficiently reflect and scatter light, minimize reflection losses (e.g., and associated energy losses) of a light beam, and dissipate heat transferred from the surface of the pathological tissue through the transmissive element 114. Such example materials include stainless steel and oxygen free copper.

A length of the cannula 102 that is sufficient for housing the optical fiber 108 also provides manipulability of the photonic device 100 (e.g., improves an case of using the photonic device 100), increases a heatsinking surface of the cannula 102, minimizes or prevents internal reflection losses, and avoids the need for special coatings that would otherwise be needed to achieve efficient coupling of light energy emitted from the optical fiber 108 to the pathological tissue. A selected length, internal diameter, and wall thickness of the main portion 122 of the cannula 102 can vary, depending on an area and/or a volume of a pathological tissue to be treated. In the depicted example embodiment of the photonic device 100 (e.g., which may be used for photonic ablation of cancerous tumors less than 2-3 cm in diameter and 1-2 cm deep), the main portion 122 has a length of about 120 mm, an internal diameter of about 7 mm, and a wall thickness of about 2 mm. The cannula 102 may take on a variety of dimensions and proportions so long as the cannula 102 is long enough to house a length of the transmissive element 114, is practically sized for handling, and is suitably sized to achieve adequate thermal management. In some embodiments, an internal surface of the cannula 102 may be characterized by control roughening to homogenize a distribution of the light intensity at a distal surface 126 of the transmissive element 114.

The transmissive element 114 is made of one or more materials that transmit light wavelengths in a range of about 400 nm to about 14 μm (e.g., including visible light energy and near infrared (NIR) light energy), that serve as adequate heat conductors, and that sink excessive heat to prevent the emitted light energy from burning the pathological tissue. Example materials from which the transmissive element 114 may be made include sapphire, diamond, calcium fluoride, and chalcogenide glasses. For example, sapphire may efficiently transmit light wavelengths in the NIR range, up to about 12 μm. The transmissive element 114 transmits the light energy emitted from the optical fiber 108 through the distal end region 116 of the cannula 102 to deliver the light energy to the pathological tissue. The transmissive element 114 also transmits heat energy generated at the pathological tissue to the cooler material of the cannula 102 according to thermal gradients created by contact between the transmissive element 114 and the cannula 102. Such thermal gradients generally depend on parameters including a structural form of the transmissive element 114, material properties of the transmissive element 114, and an arrangement of the transmissive element 114 with respect to the cannula 102. Heat energy is safely radiated or conducted from the cannula 102 to other thermally conductive surfaces (e.g., the metal jacket of the optical fiber 108).

In some embodiments, the transmissive element 114 is coated (e.g., brazed) with a metalized substance (e.g., silver, gold, or oxygen free copper) to maximize thermal contact between the transmissive element 114 and the cannula 102. In some embodiments, the transmissive element 114 is not coated with such a metalized substance. For example, the transmissive element 114 may be adhered to an inner surface of the cannula 102 with a thermally conductive adhesive substance (e.g., an epoxy substance). In some embodiments, the transmissive element 114 can be attached to the inner surface of the cannula 102 without an adhesive substance, but with a press fit, to improve surface contact between the transmissive element 114 and the cannula 102 and thereby improve heat dissipation.

The transmissive element 114 is a cylindrical structure with an aspect ratio of less than one for optimal heat transfer from a distal surface 126 of the transmissive element 114 to the cannula 102. For example, the transmissive element 114 typically has a length of about 45 mm to about 55 mm (e.g., about 50 mm) and a diameter of about 5.9 mm to about 6.1 mm (e.g., about 6.0 mm). In some embodiments, the transmissive element 114 has a fine, uniform diffuser polish along the distal surface 126 and a 40/60 scratch and dig quality along the proximal surface 128. The diffuser polish can improve the uniformity of the light intensity distribution through the transmissive element 114, thereby eliminating hot spots and making heat deposition and distribution at the surface of the pathological tissue (i.e., which in contact with the distal surface 126 of the transmissive element 114) more uniform. The scratch and dig finish can eliminate or significantly minimize large pits or scratches in the proximal surface 128 that would otherwise affect both the efficiency of light transmission from the optical fiber 108 to the pathological tissue, as well as the light intensity distribution at the surface of the pathological tissue, which would ideally have a perfectly uniform intensity. In some embodiments, the uniform diffuser polish and the scratch and dig finish may be located on opposite sides of the transmissive element 114. In some embodiments, the transmissive element 114 may not include either or both of the diffuser polish and the scratch and dig surface finishes.

In some embodiments, either or both of the distal and proximal surfaces 126, 128 of the transmissive element 114 may be coated with an anti-reflection (AR) coating at an appropriate light wavelength to minimize reflections of the laser light emitted from the optical fiber 108. In some embodiments, the distal surface 126 of the transmissive element 114 may be coated with materials (e.g., diamond) that both improve thermal contact with the pathological tissue and improve thermal transmission from the pathological region to the transmissive element 114 with minimal or no impact to the transmission of light energy through the transmissive element 114. Additionally, in some embodiments, the transmissive element 114 extends past the distal end region 116 of the cannula 102 by about 1.0 mm to about 3.0 mm (e.g., about 2.0 mm) to limit between the cannula 108 and the pathological tissue.

Still referring to FIGS. 1 and 2, the optical fiber 108 is coupled to a light source (not shown), transmits light energy emitted from the light source, and emits the light energy towards the transmissive element 114. The optical fiber 108 is typically made of one or more materials, including fused quartz and fused silica. In some embodiments, the light source is a laser. In such embodiments, the optical fiber 108 may have a numerical aperture (NA) of 0.22 and be designed to produce a uniform intensity beam profile. For example, the optical fiber 108 may produce uniform intensity beams profiles with a circular cross-sectional shape, a hexagonal cross-sectional shape, a square cross-sectional shape, or any other suitable uniform intensity shape. During operation of the photonic device 100, a temperature of the pathological tissue being treated increases as a function of time that the light source is activated, while the thermally conductive surfaces of the cannula 102, the tube 104, and the male connector 106 dissipate heat transmitted from the surface of the pathological tissue through the transmissive element 114. Therefore, the temperature at the surface of the pathological tissue remains substantially constant over time.

The optical fiber 108 extends distally into the main portion 122 of the cannula 102 such that a beam area of the emitted light is about 60% to about 80% of an area of the distal surface 126 of the transmissive element 114. For example, the output end 130 of the optical fiber 108 is typically spaced from the proximal surface 128 of the transmissive element 114 by a distance of about 0.1 cm to about 1.0 cm. In an example embodiment where the optical fiber 108 has a 0.22 NA and a clear aperture of 8 mm, the output end 130 of the optical fiber 108 may be spaced about 3 mm from the proximal surface 128 of the transmissive element 114. The fiber support member 110 defines a central longitudinal opening 132 that supports and centers the optical fiber 108 within the cannula 102. The fiber support member 110 may be attached to an internal surface of the cannula 102 with an adhesive substance (e.g., an epoxy substance). Example materials from which the fiber support member 110 and may be made include as polylactic acid (PLA), stainless steel, and polytetrafluoroethylene (PTFE). The fiber support member 110 may be embodied as a grommet, a washer, a hollow cylinder, or another similar structure.

Figures 3, 4, 5:
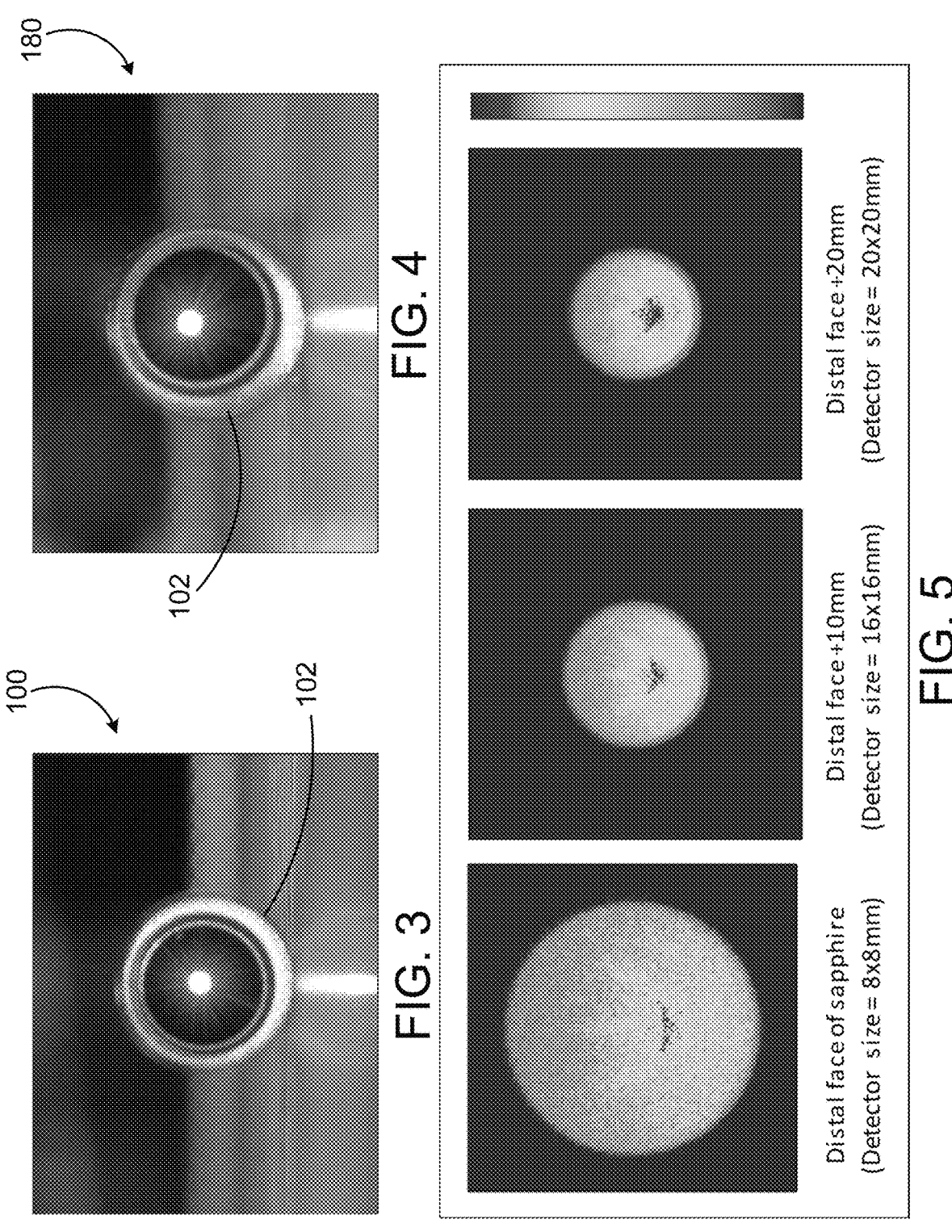
FIG. 3 is an end view of the photonic device of FIG. 1, showing a centered light source.
FIG. 4 is an end view of a photonic device, showing an off-center light source.
FIG. 5 is a set of images of a distal surface of a transmissive element of the photonic device of FIG. 4, acquired at varying distances from the distal surface.

FIGS. 3 and 4 respectively illustrate end views of the photonic device 100 (e.g., including the fiber support member 110 adhered to the cannula 102) and another photonic device 180 (e.g., a visible laser) that is similar in construction and function to the photonic device 100, except that the photonic device 180 does not include the fiber support member 110. Accordingly, the photonic device 180 includes the other components of the photonic device 100. The decentering effects of omitting the fiber support member 110 can be clearly seen in FIG. 4. For example, despite a stiffness of the optical fiber 108, the optical fiber 108 extends into the cannula 102 at an off-axis (e.g., off-center) orientation (e.g., up to about 3 mm away from an axis of the cannula 102)

without centering provided by the fiber support member 110. Detectors placed at the distal surface 126 of the transmissive element 114, at a first distance of about 10 mm from the distal surface 126, and at a second distance of about 20 mm from the distal surface 126 produce the images shown in FIG. 5, which illustrate the off-axis position of the output end 130 of the optical fiber 108 within the cannula 102 of the photonic device 180.

Other embodiments of photonic devices that are similar to the photonic device 100 in construction and/or function are possible. For example, while the photonic device 100 has been described and illustrated as having a configuration in which the optical fiber 108 extends distally into the cannula 102, in some embodiments, a photonic device that is similar in function to the photonic device 100 may include one or more different features or configurations, such as imaging lenses that relay light energy to a distal surface of a sapphire rod (e.g., thereby completely eliminating internal reflection losses in a cannula) or such as lacking the optical fiber 108 altogether in lieu of a light source (e.g., a light-emitting diode (LED)) inside of a cannula at an appropriate distance from a sapphire rod.

Figures 6, 7:
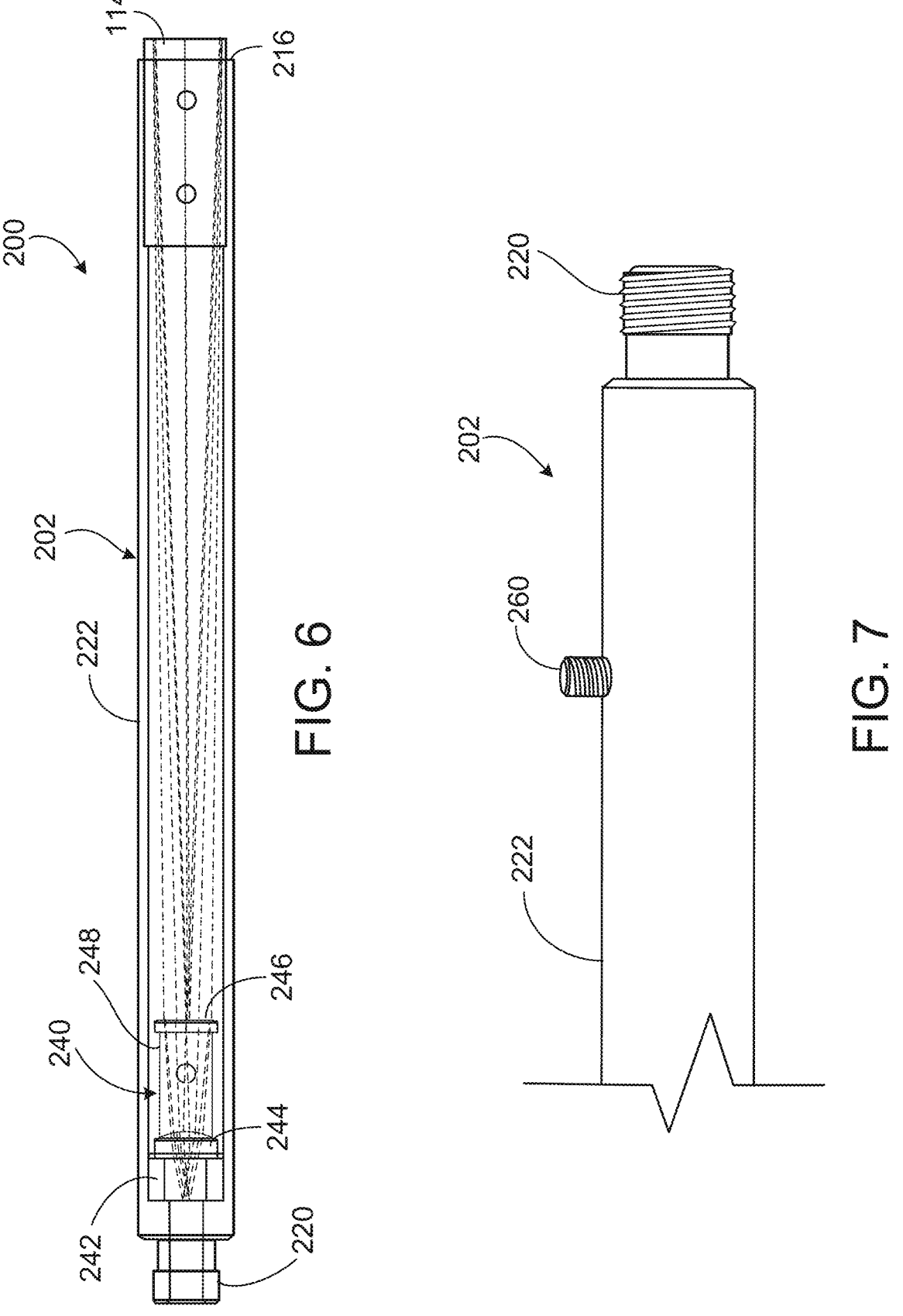
FIG. 6 is a cross-sectional view of a portion of a photonic device that includes imaging lenses housed within a cannula.
FIG. 7 is a perspective view of a portion of the cannula of the photonic device of FIG. 6.

For example, FIG. 6 illustrates an internal side view of a portion of a photonic device 200 (e.g., a non-ablative laser) that includes a lens assembly 240 for imaging (e.g., relaying) light energy from an output end (e.g., a distal end) of an optical fiber (not shown) to a surface of a pathological tissue (e.g., located at the distal surface 126 of the transmissive element 114) without incurring reflection losses at a surface of a cannula 202. Like the photonic device 100, the photonic device 200 is designed to deliver photonic therapy to a pathological tissue in a mammal. That is, the photonic device 200 can deliver photonic therapy to particles bound to the pathological tissue or deliver photonic therapy directly to the pathological tissue. The photonic device 200 includes the cannula 202 and the transmissive element 114 of the photonic device 100. The photonic device 200 also includes a fiber optic cable assembly (not shown) that is similar to the fiber optic cable assembly 104 of the photonic device 100, including the tubular housing 118, the optical fiber 108, and the male connector 106, except that the optical fiber 108 does not extend as far distally past the male connector 106 as compared to the fiber optical cable assembly 104. Such a configuration permits the optical fiber 108 to be inserted and terminate within a female connector 220 that forms a proximal end of the cannula 202 (e.g., as opposed to extending distally within a main portion 222 of the cannula 202). FIG. 7 illustrates a perspective view of a portion of the cannula 202. The cannula 202 is substantially similar in construction and function to the cannula 102 of the photonic device 100, except that the cannula 202 includes a port 260 that facilitates assembly of the lens assembly 240 with the cannula 202, as will be discussed in more detail below.

Referring again to FIG. 6, in the depicted embodiment, the lens assembly 240 includes a cylindrical support base 242, a proximal lens 244, a distal lens 246, and a spacer 248 that secures the lenses 244, 246 at fixed positions within the cannula 202. For example, the lenses 244, 246 may be bonded to an inner surface of the spacer 248 with a suitable bonding agent, such as a suitable epoxy adhesive. The cylindrical support base 242 delivers the light energy emitted from the optical fiber 108 to the proximal lens 244 and defines a distance between the output end 130 of the optical fiber 108 and the proximal lens 244. The cylindrical support base 242 may have a length of about 20 mm to about 400 mm (e.g., about 120 mm) and may be made of one or more materials including stainless steel, oxygen free copper, aluminum, and other materials.

The output end 130 of the optical fiber 108 (not shown) is fixed in position relative to the lens 242 by the SMA connector design provided by the male connector 106 (not shown) and the female connector 220. In the example embodiment of the photonic device 200, the transmissive element 114 does not include the fine diffuser polish and the 40/60 scratch and dig quality of the end surfaces 126, 128 to achieve a uniform light intensity profile. Instead, the lens assembly 240 is designed to relay the uniform light intensity profile generated by the fiber coupled light source to the distal surface 126 of the transmissive element 114. Design parameters (e.g., lens focal lengths, separation between lenses, etc.) of the lens assembly 240 can be used to tailor a shape of the light beam and/or an intensity distribution at the surface of the pathological tissue as needed to maximize the effectiveness of the photonic therapy (e.g., to produce a square beam shape with a significantly uniform intensity distribution).

The lenses 244, 246 have focal lengths and positions along the cannula 202 that are appropriate for imaging the distal end of the optical fiber onto the distal surface 126 of the transmissive element 114. The lenses 244, 246 typically include an anti-reflective (AR) coating to minimize reflection losses. The spacer 248 may be made of a resin or one or more other materials. The spacer 248 may be fixed in position with respect to the cannula 202 by a fastener (e.g., a set screw) disposed within the port 260 of the cannula 202.

Inclusion of the lenses 244, 246 within the photonic device 200 facilitates tuning of both a size and a shape of the light beam profile at a surface of a pathological tissue such that a uniform intensity distribution is delivered to the pathological tissue. For example, inclusion of the lenses 244, 246 increases a transmission efficiency of light energy exiting the optical fiber and relayed to a pathological surface as compared to similar devices without such lenses. The lenses 244, 246 also allow the emitted laser beam to penetrate the pathological tissue to reach a depth (e.g., up to about 2 cm) greater than a depth (e.g., up to about 6 mm) that can be treated with conventional devices without burning a surface of the pathological tissue at which the photonic device 200 is directed by imaging the optical fiber onto the pathological tissue. Because a uniform thermal distribution is produced, more power can be applied without burning the pathological tissue such that adequate photonic energy can be delivered to the pathological tissue at greater depths. In this manner, the photonic device 200 can deliver photonic therapy to the pathological tissue to destroy the pathological tissue from the bottom up without burning the surface, thereby influencing a thermal gradient within the pathological region. In some implementations, power in a range of about 1 W to about 15 W may be input to the photonic device 200.

Figures 8, 9:
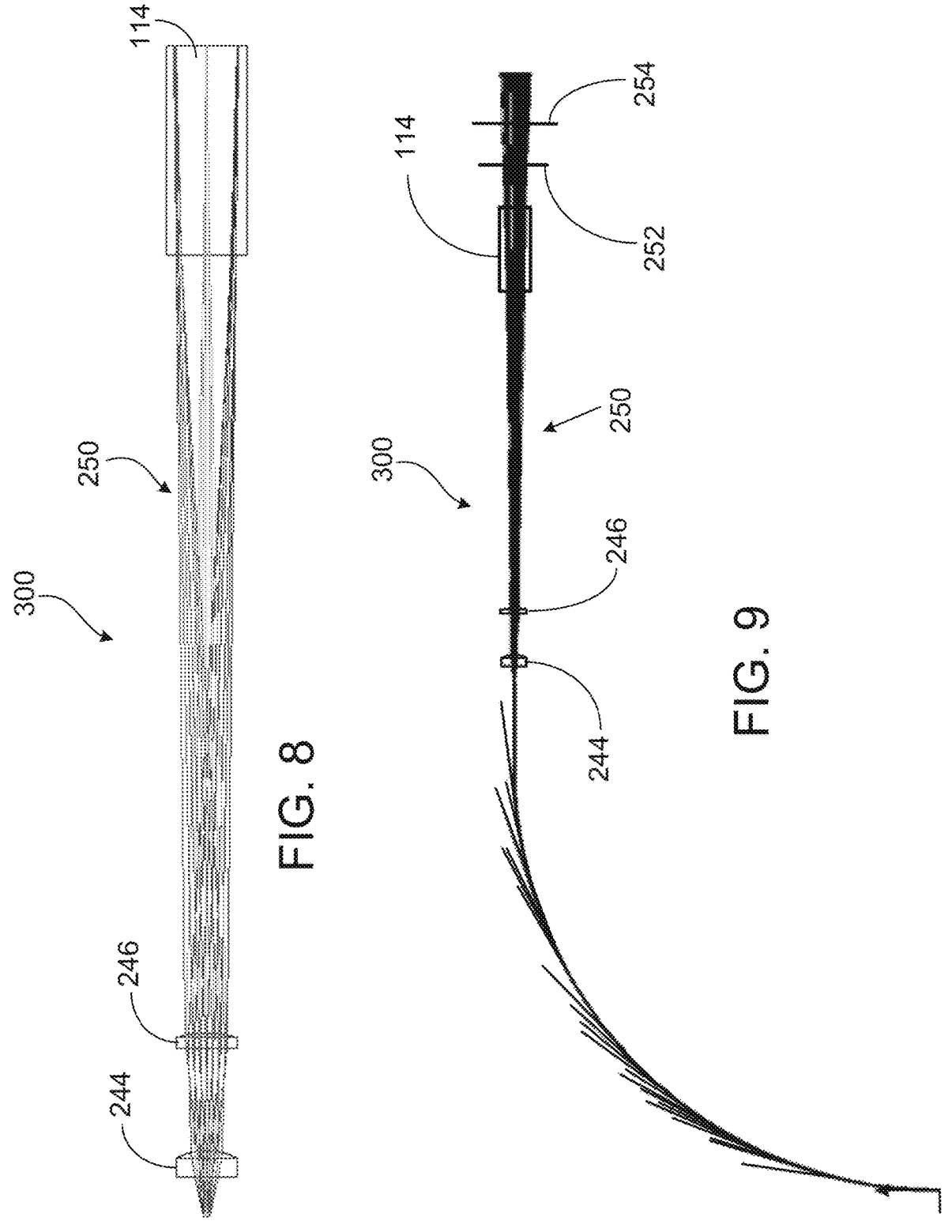
FIG. 8 is a partial schematic of a sequential ray trace of a light beam transmitted through optical elements of a photonic device including a lens assembly.
FIG. 9 is a full schematic of the sequential ray trace of FIG. 8, inclusive of a path along a fiber optic cable assembly.

FIGS. 8 and 9 respectively illustrate a partial schematic (e.g., excluding a path along a fiber optic cable assembly) and a full schematic (e.g., including the path along the fiber optic cable assembly) of an example optical design and example ray traces 250. The ray traces 250 show a light source transmitted through a photonic device 300 that is substantially similar in construction and function to the photonic device 200 of FIG. 5, except that the photonic device 300 includes an optical fiber that produces a uniform hexagonal light intensity distribution profile. For example, the photonic device 300 includes several components of the photonic device 200 (e.g., the cannula 202, the lens assembly 240, and the transmissive element 114), some of which are not shown in FIGS. 8 and 9. The optical fiber of the photonic device 300 has a 0.22 NA and a cross-sectional width (e.g., a core diameter) of about 600 μm. The lens assembly 240 (lenses 244, 246 shown in FIGS. 8 and 9) images the intensity profile distribution at the distal end of the optical fiber (i.e., located adjacent the proximal lens 244) onto the distal surface 126 of the transmissive element 114. Images may be acquired of the distal surface 126 of the transmissive element 114 at various distances from the transmissive element 114, as indicated by positions 252, 254 in FIG. 9.

Figures 10, 11, 12:
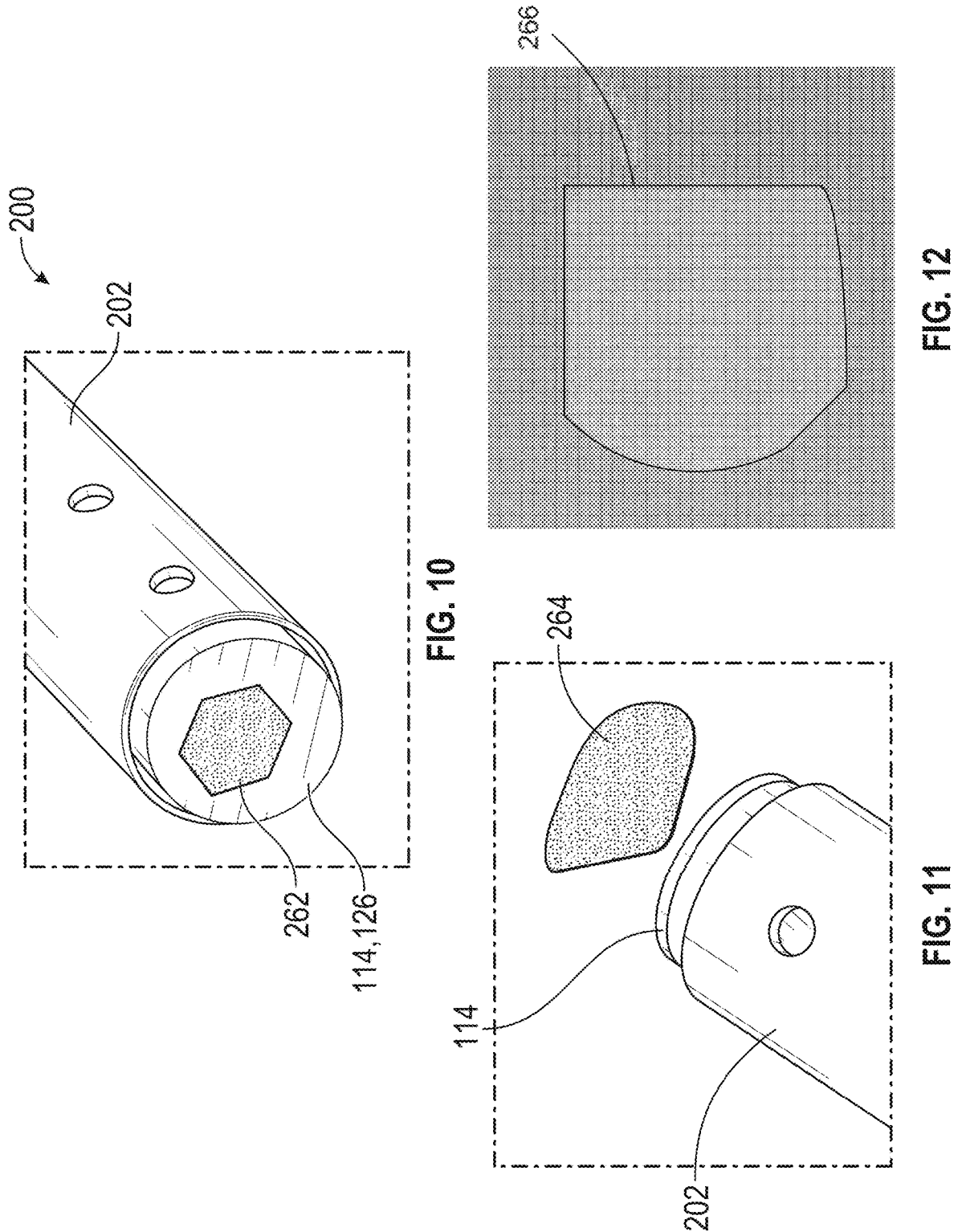
FIG. 10 is an image associated with a ray trace and optical design configuration of FIGS. 8 and 9, exemplifying proper design and adequate alignment (e.g., a near central alignment) using a hexagonal core fiber, and delivering a uniform irradiance at a distal surface of a conductive element positioned along a distal end region of a cannula.
FIG. 11 is an image of a distal surface of a conductive element positioned along a distal end region of a cannula and a light irradiance profile positioned a few millimeters from the distal surface.
FIG. 12 is an expanded view of the light irradiance profile of FIG. 11, omitting the cannula.

FIG. 10 illustrates an image 262 of the cross-sectional shape of the hexagonal uniform intensity distribution generated on the distal surface 126 of the transmissive element 114 of the photonic device 300 described with respect to FIGS. 8 and 9. FIGS. 11 and 12 illustrate images 264, 266 of the light intensity distribution generated on a plane spaced apart from the distal surface 126 of the transmissive element 114 of different photonic devices producing square and circular cross-sectional shapes, respectively. Such photonic devices are substantially similar in construction and function to the photonic device 300, except that the devices respectively include optical fibers with square and circular cross-sectional shapes associated with the images 264, 266. Off-center positions of the images 262, 264, 266 can result from slack (e.g., lose tolerances) between the cannula 202 and the spacer 248.

Figures 13, 14, 15:
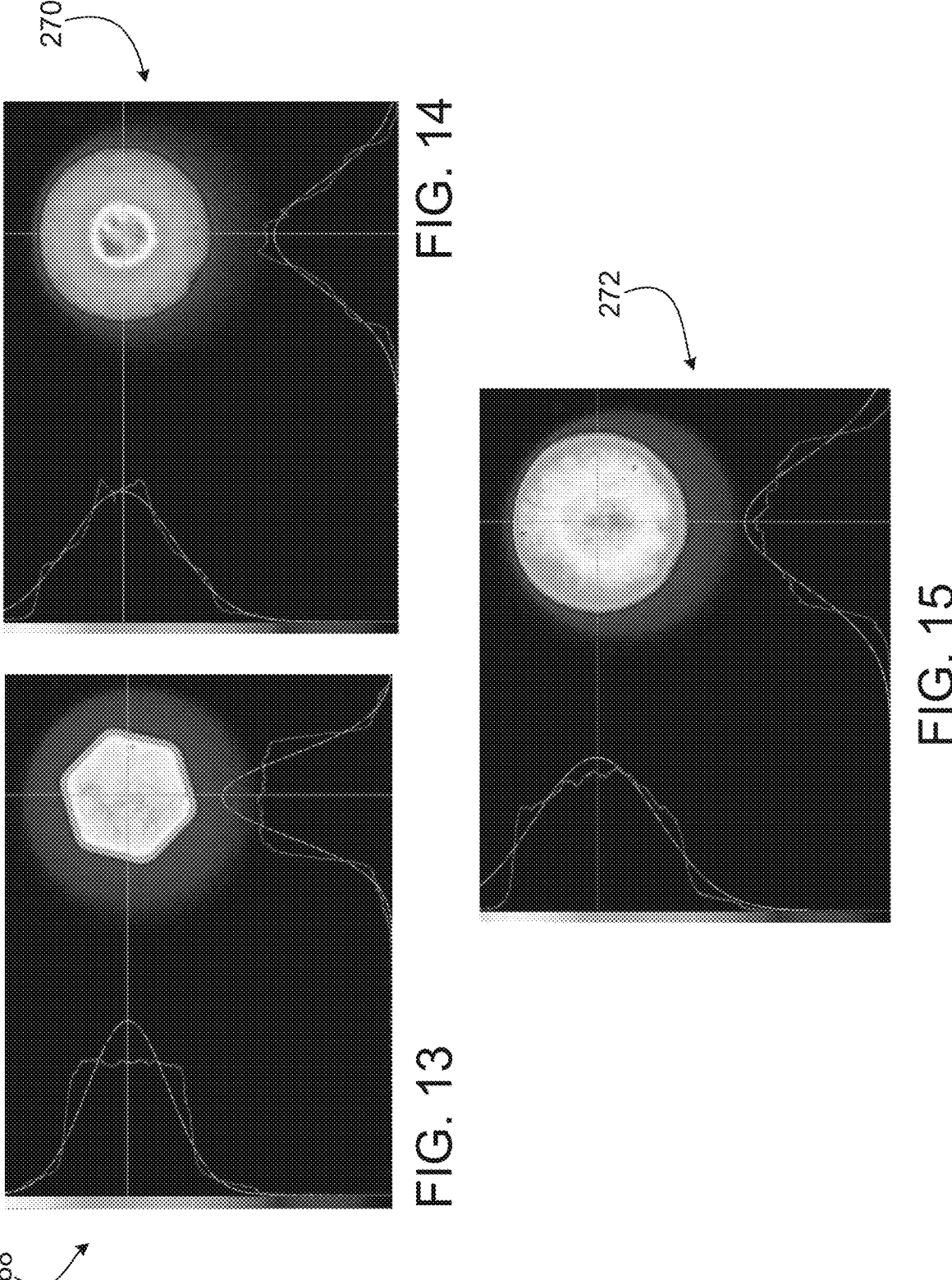
FIG. 13 is a beam intensity profile of the irradiance distribution of the beam exiting the cannula and corresponding to the image shown in FIG. 10.
FIG. 14 is a beam intensity profile showing sub-optimal, non-uniform irradiance that is potentially inadequate for photonic therapy.
FIG. 15 is a beam intensity profile showing sub-optimal, non-uniform irradiance that is potentially inadequate for photonic therapy.

FIG. 13 illustrates a measured intensity distribution of a light profile 268 resulting from the photonic device 300 employing a hexagonal cross-sectional shape generating optical fiber and properly designed imaging optics (e.g., the lenses 244, 246). In contrast to the uniform intensity distribution 268, and as shown in FIG. 14, a conventional optical fiber (i.e., absent any light intensity homogenization) or inadequately diffused or homogenized light from any optical fiber produces a non-uniform intensity profile, such as a non-uniform intensity profile 270, that peaks along a center of the laser beam and decreases with a distance from the center of the laser beam. In other examples, such a conventional optical fiber may produce a non-uniform intensity profile, such as a non-uniform intensity profile 272 shown in FIG. 15, that exhibits high intensity regions. The high intensity central area of Gaussian intensity profiles or the high peak irradiance areas of inadequately diffused light beams can easily have local intensity (e.g., peak irradiances that are many times that of the average intensity of the light beam, defined as a total power of the light beam divided by a beam area), which can result in non-uniform warming of the pathological tissue.

In contrast, uniform intensity light distributions have substantially equal peak and average irradiances characterized by a substantially constant intensity, such that a pathological tissue irradiated by the light can be uniformly treated. The substantially constant irradiance of the light profile 268 results in a gentle, uniform warming of the pathological tissue. In this manner, carbonization of the pathological tissue by high intensity peak irradiance areas can be avoided, whereas conventional devices are intentionally designed to carbonize tissue. In this manner, an entire surface area illuminated by the photonic device 300 can be adequately treated with an optimized therapy.

The photonic devices 100, 200, 300 are non-invasive devices that can deliver photonic therapy to accessible pathological tissues. Such accessible pathological tissues may be located on skin or within a body cavity (e.g., such as oral and vaginal cavities). Example pathological tissues include melanomas and mast cell carcinomas in humans and dogs, fibrosarcomas in cats, and, in general, non-invasively or minimally invisibly accessible pathological tissues of the type that could be treated cryogenically or through surgical excisions. In operation of the photonic devices 100, 200, 300, a pathological tissue can be treated (e.g., systemically via an intravenous injection, or locally at a tumor or its main blood supply) with a dosage of nanoparticles such that the nanoparticles accumulate on and/or within the pathological tissue at a desired concentration, and do so preferentially in cancerous tissues as these are highly vascularized. After a predetermined wait period of about 12 hours to about 36 hours to allow for the diffusion of nanoparticles into the pathological tissue, the photonic devices 100, 200, 300 can be positioned in contact with the surface of the pathological tissue and controlled (e.g., monitoring a surface temperature of the pathological tissue) to deliver 808 nm laser energy with a continuously delivered dosage of about 2 W/cm$^2$ to about 20 W/cm$^2$ for a duration of about 5 min to the pathologic site. Delivery of the laser dosage causes the nanoparticles to heat to a temperature in a range of about 45° C. to about 55° C., where such heating preferentially destroys the pathological tissue without harming surrounding healthy tissues.

FIG. 16 illustrates an example process 400 for delivering photonic therapy to a pathological region. In some implementations, the method includes emitting light energy from a first optical element within a cannula (402). In some implementations, the method further includes producing a substantially uniform irradiance profile from the light energy within the cannula (404). In some implementations, the method further includes transmitting the light energy emitted from the first optical element through a second optical element in thermal contact with a distal end of the cannula to the pathological tissue without ablating the pathological tissue (406). In some implementations, the method further includes conducting thermal energy from the pathological tissue through the second optical element and to the cannula (408).

A number of embodiments have been described. Nevertheless, it will be understood that various modifications may be made without departing from the spirit and scope of the disclosure. For example, while the photonic devices 100, 200, 300 have been described and illustrated as including the transmissive element 114, in some embodiments, a photonic device that is similar in function to either of the photonic devices 100, 200, 300 may not include a rod, but use an actively cooled window. In some implementations, such a photonic device may be more efficient (e.g., may emit a relatively high portion of electromagnetic energy input to the cannula assembly).

While components of the photonic devices 100, 200, 300 have been described and illustrated as including certain dimensions, shapes, and material formulations, in some embodiments, a photonic device that is similar in construction and function to either of the photonic devices 100, 200, 300 may include one or more components that have different dimension, shapes, and/or material formulations.

In some implementations, any of the photonic devices 100, 200, 300 may be used in conjunction with other forms of electromagnetic energy. For example, concurrent application to the pathological tissue of the photonic energy and electromagnetic fields generated by direct or alternating current, direct or pulsed electric currents, or radio frequency would reduce the photonic energy needed to produce the desired therapeutic effect on the pathological tissue. Thus, such combinations would either enhance the depths at which the photonic energy would produce the desired effect and/or reduce the intensity of the photonic energy needed at the surface of the pathological tissue.

In some implementations, using any of the photonic devices 100, 200, 300 in conjunction with properly selected materials that optimize energy transfer between the transmissive element 114 and the surface of the pathological tissue (e.g., water, ultrasound gel, etc.) can produce a more intimate contact between the surface and minimize losses of the photonic energy due to index of refraction mismatches between a material of the transmissive element 114 and the pathological tissue. Additionally, by eliminating air gaps between the transmissive element 114 and the pathological tissue, such materials can act to more efficiently couple heat from the pathological tissue to the transmissive element 114 for radiative and/or conductive dissipation by the cannula. In some embodiments, the materials may additionally be infused with an analgesic agent (e.g., lidocaine) to minimize patient discomfort.

In some implementations, using any of the photonic devices 100, 200, 300 in conjunction with a cooling source (e.g., a cold air blower, thermos-electrically actively cooled cannula surface, etc.) may maximize the photonic energy that can be delivered to the pathological tissue without tissue carbonization.

In some implementations, the photonic devices 100, 200, 300 may be used to deliver photonic therapy directly to a pathological tissue (e.g., without nanoparticles). In some implementations, a single photonic device 100, 200, 300 may be operated sequentially at different locations along the pathological tissue until a complete area of the pathological tissue is treated.

Figure 17:
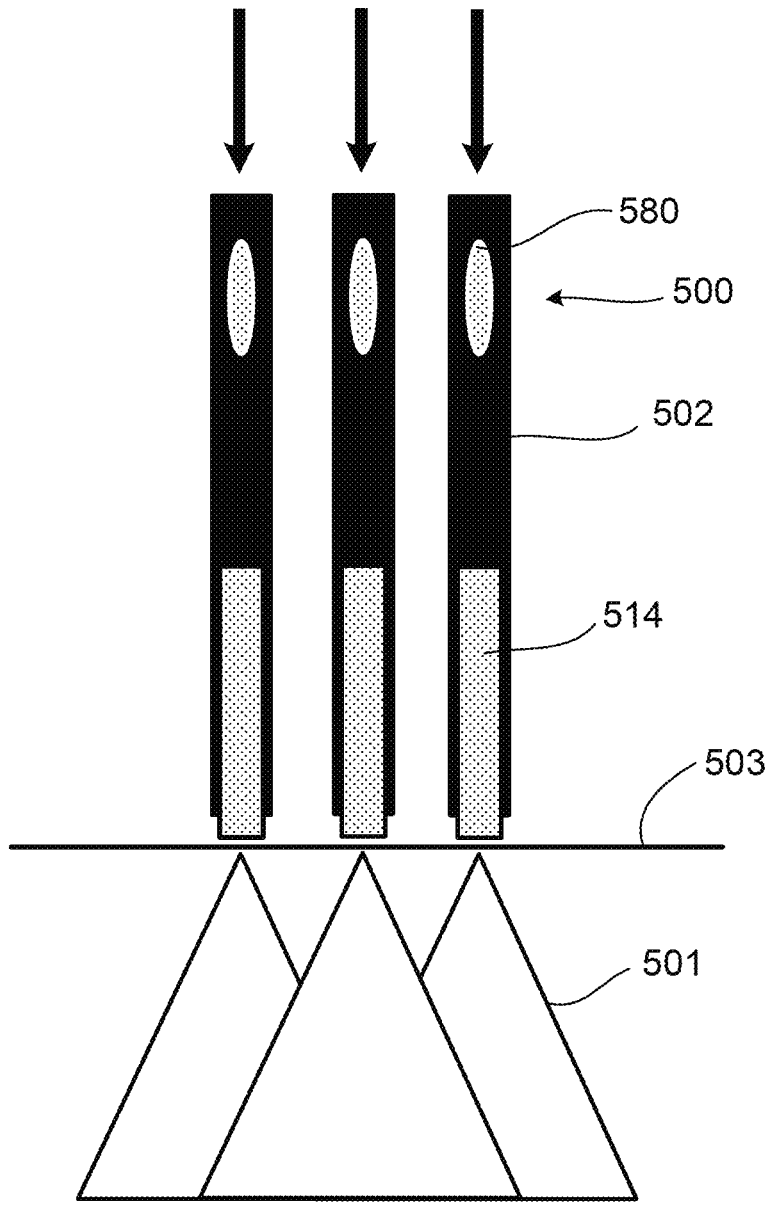
FIG. 17 is a cross-sectional view of multiple photonic devices arranged adjacent one another to deliver overlapping light beams at a depth below a surface of a pathological tissue.

In other instances, multiple photonic devices 100, 200, 300 may be positioned adjacent one another and operated in parallel (e.g., at the same time) to treat a large region of a pathological tissue. For example, FIG. 17 illustrates multiple photonic devices 500 (e.g., embodied as any of the photonic devices 100, 200, 300) arranged adjacent one another to deliver multiple light beams 501 to a pathological tissue. The photonic devices 500 receive input light and format the input light with one or more optical elements 580 (e.g., embodied as the optical fiber 108 or the lenses 244, 246). Although the light beams 501 do not overlap at distal surfaces of the transmissive elements 514 (e.g., at output ends of the cannulas 502), the light beams 501 do overlap at a depth below a surface 503 of the tissue. Such overlap will produce greater heating at a target area below the surface 503 of the tissue than could a single photonic device alone. Accordingly, in some embodiments, distal features of the cannula 502 may be sharp such that a distal end of the photonic device 500 can be inserted into a tissue to produce any desired thermal profile at any depth of the tissue.

In some embodiments, the cannula of any of the photonic devices 100, 200, 300 or of a photonic device that is similar in construction and function to any of the photonic devices 100, 200, 300 may be actively cooled to increase irradiance at a pathological tissue without being limited by thermal characteristics of the transmissive element or the ambient environment such that the maximum heat that the cannula can dissipate can be controlled. For example, the cannula may be actively cooled using one or more of chilled water, thermos electric cooling technology, heat pipes, and phase change materials.

What is claimed is:

1. A method of delivering light energy to the pathological tissue of a mammal at the skin or other external tissue, the method comprising:

emitting first light energy from a first optical element;

producing a substantially uniform first irradiance profile from the first light energy;

transmitting the first light energy along a first optical path from the first optical element through a distal end surface of a second optical element directly, and in a first axial direction, to a surface of the pathological tissue in a non-invasive manner without ablating the pathological tissue;

emitting second light energy from a third optical element;

producing a substantially uniform second irradiance profile from the second light energy; and transmitting the second light energy along a second optical path from the third optical element through a distal end surface of a fourth optical element directly, and in the first axial direction, to the surface of the pathological tissue in a non-invasive manner without ablating the pathological tissue;

wherein the first light energy and the second light energy do not overlap one another at the surface of the pathological tissue and do overlap one another at a depth below the surface of the pathological tissue.

2. The method of claim 1, wherein the first optical element and/or the third optical element comprises an optical fiber and the second optical element and/or the fourth optical element is in direct, non-invasive contact with the surface of the pathological tissue.

3. The method of claim 1, wherein the second optical element and/or the fourth optical element comprises a cylindrical sapphire rod.

4. The method of claim 1, further comprising generating the first light energy and/or the second light energy with a laser.

5. The method of claim 1, further comprising generating the first light energy and/or the second light energy with a light-emitting diode (LED).

6. The method of claim 1, wherein the first irradiance profile and/or the second irradiance profile has a non-circular cross-sectional shape.

7. The method of claim 1, wherein the first irradiance profile and/or the second irradiance profile has a hexagonal cross-sectional shape or a square cross-sectional shape.

8. The method of claim 1, further comprising directing the first light energy through one or more lenses positioned between the first optical element and the second optical element.

9. The method of claim 8, further comprising directing the second light energy through one or more lenses positioned between the third optical element and the fourth optical element.

10. The method of claim 1, further comprising:

delivering nanoparticles to the pathological tissue such that the nanoparticles accumulate at the pathological tissue;

transmitting the first light energy and the second light energy to the nanoparticles at the pathological tissue; and heating the nanoparticles with the first light energy and the second light energy to destroy the pathological tissue without harming healthy tissue adjacent to the pathological tissue.

* * * * *